United States Patent [19]

Hotta

[11] Patent Number: 4,588,777

[45] Date of Patent: May 13, 1986

[54] SYNTHETIC RESIN COMPOSITION

[75] Inventor: Masahiro Hotta, Matsudo, Japan

[73] Assignee: Dainippon Plastics Co., Ltd., Osaka, Japan

[21] Appl. No.: 544,146

[22] Filed: Oct. 21, 1983

[30] Foreign Application Priority Data

Oct. 21, 1982 [JP] Japan .................. 57-185874

[51] Int. Cl.⁴ .............................. C08L 53/02
[52] U.S. Cl. ...................... 525/93; 604/408; 525/98; 525/227
[58] Field of Search ................ 525/93; 604/408

[56] References Cited

U.S. PATENT DOCUMENTS

| | | | |
|---|---|---|---|
| 3,433,573 | 3/1969 | Holladay | 525/227 |
| 3,562,356 | 2/1971 | Nyberg | 525/93 |
| 4,140,162 | 2/1979 | Gajewski et al. | 150/1 |
| 4,440,815 | 4/1984 | Zomorodi | 525/93 |

*Primary Examiner*—John C. Bleutge
*Assistant Examiner*—Patricia A. Short
*Attorney, Agent, or Firm*—Armstrong, Nikaido, Marmelstein & Kubovcik

[57] ABSTRACT

A synthetic resin composition comprising (a) a hydrogenated block-copolymer of an aromatic vinyl compound such as styrene and a conjugated diene compound such as butadiene and isoprene, (b) an ethylene-acrylate copolymer and (c) an isotactic propylene or its copolymer, which is non-toxic and superior in softness, transparency, high-temperature strength and molding characteristic, and is useful for preparing food-packings or medical appliances.

8 Claims, 1 Drawing Figure

SYNTHETIC RESIN COMPOSITION

BACKGROUND OF THE INVENTION

1. Field of the Invention

The present invention relates to a synthetic resin composition. More particularly, it relates to a synthetic resin composition comprising a hydrogenated block-copolymer of an aromatic vinyl compound and a conjugated diene compound, and polyolefinic compounds which is non-toxic and superior in softness, transparency, high-temperature strength and molding-characteristic.

2. Brief Description of the Prior Art

Hitherto, various synthetic resin compositions for molding have been proposed and practically used to obtain transparent and soft mold goods in the field of food packing material, medical appliances and the like. However, these known synthetic resin compositions all have such problems as described below.

That is, mold goods prepared from ethylene/vinyl acetate copolymer, ethylene/acrylate copolymer, 1,2-polybutadiene, metal salt of ethylene/acrylic acid or methacrylic acid copolymer, or the like are favorable in softness and transparency, but have problems that their tensile strengh is only 200 kg/cm$^2$ or less and their thermal resistance is so insufficient that they cannot keep their shape at a temperature of 100° C. or lower because of softening. Therefore, these mold goods have a defect that they cannot be sterilized by heating at a high temperature. Although thermoplastic polyurethane and thermoplastic polyester are superior in softness, tensile strength and thermal resistance, their transparency is not necessarily sufficient and moreover they have such defect that they are expensive and sanitary problems arise if their monomer remains. Elastomers of silicone series also are very expensive, though they are superior in softness, tensile strength and thermal resistance and have good transparency.

Further, it is known that mold goods based on such thermoplastic elastomers as styrene/butadiene block copolymer, styrene/butadiene/styrene block copolymer, styrene/isoprene/styrene block copolymer and the like are superior in softness and transparency and have a tensile strength of 200 kg/cm$^2$ or more. However, they also have a problem that their thermal resistance is insufficient and so they cannot keep their shape even at a temperature of 100° C. or lower because of softening.

To improve said copolymers with regard to this problem, hydrogenated block copolymers of styrene/-butadiene/styrene block copolymer or styrene/isoprene/butadiene copolymer have been proposed and put on the market recently. These hydrogenated block copolymers are superior in softness, transparency and tensile strength. However, their thermal resistance is still insufficient though it is considerably improved as compared with that of unhydrogenated ones. Further, they are abnormal in their fluid-characteristic in the molten state and inferior in their molding-characteristic, especially, extrusion molding-characteristic. Therefore, in the field of engineering plastics, they are used mainly for the purpose of improving other resins by adding thereto in a small amount (cf. U.S. Pat. Nos. 4,081,424, 4,080,357, 4,111,896, 4,080,356, 4,090,996, 4,111,895, 4,088,627 and 4,088,626).

One exceptional example of using said hydrogenated block copolymers as the main component is their composition with polypropylene and ethylene-vinylacetate copolymer (cf. U.S. Pat. No. 4,140,162), which however is insufficient in softness at a low temperature, strength at a high temperature and the like.

Thermoplastic elastomers of ethylene/propylene copolymer series or those based on ethylene/propylene copolymer and polypropylene are soft and their thermal resistance is relatively good. However, they are considerably inferior in transparency and tensile strength.

In contrast, molding goods prepared from soft polyvinyl chloride are superior in softness and transparency, have a tensile strength of such degree as 200 kg/cm$^2$, and keep their shape even at a high temperature of such degree as 120° C. while maintaining sufficient strength. Therefore, they can be sterilized by heating at a high temperature and are widely used not only in the field of general packing industry but also for food packing, medical appliances and the like. However, soft polyvinyl chloride usually contains a large quantity of plasticizer and is hardened by slow release of the plasticizer. Thus, it is feared that sanitary problems arise by transfer of the plasticizer into the contents in contact with packing bags, tubes of the like made of such soft polyvinyl chloride. Further, there was a fear of sanitary problems arising unless the amount of vinyl chloride monomer remaining in the mold goods could extremely be diminished.

Thus there has been an earnest desire for synthetic resins for molding, which are sufficient in softness, strength, thermal resistance and transparency, which do not contain such highly toxic plasticizer and monomer as the soft polyvinyl chloride does, and which have good molding-characteristic.

The present invention has been made to solve the above-mentioned subject that could hardly be solved by previously known resin compositions.

Thus, it has been found that substantially non-toxic synthetic resin compositions which are sufficient in softness, strength, thermal resistance and transparency and have good molding-characteristic can be obtained by using a hydrogenated block copolymer which has been hitherto used in a relatively small amount for improving other resins, as the main component of the compositions, in combination with a specific resin of polypropylene series and also with a specific ethylene/acrylate copolymer.

SUMMARY OF THE INVENTION

The present invention is to provide synthetic resin composition comprising (a) 30 to 90% by weight of a block copolymer whose both terminal blocks comprise a polymer of an aromatic vinyl compound and whose intermediate block comprises a polymer of conjugated diene series, said terminal blocks constituting 10 to 40% by weight of the copolymer and being hydrogenated in a ratio of 10% or less and said intermediate block constituting 90 to 60% by weight of the copolymer and being hydrogenated in a ratio of 90% or more, (b) 5 to 40% weight of an isotactic polyprolylene or a copolymer comprising such isotactic polypropylene as its main component having a melting point of 150° C. or higher and (c) 5 to 40% by weight of an ethylene/acrylate copolymer whose acrylate content is 5% or more.

Figure 1:
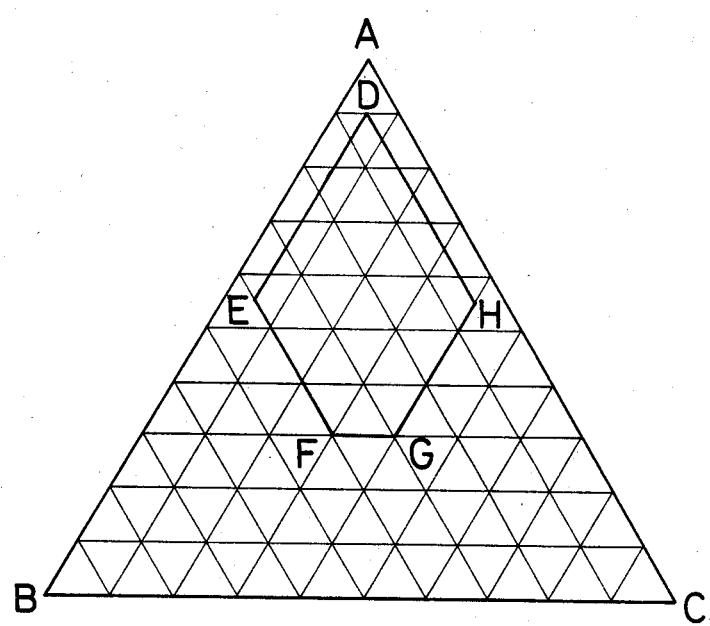
FIG. 1 is a triangular coordinates graph showing the composition range of the synthetic resin compositions of the present invention. In this Figure, the vertexes A, B and C represent the single composition (100% by weight) of the block copolymer of the present invention [the constituent (a)], the polymer of polypropylene series [the constituent (b)] and the ethylene/acrylate copolymer [the constituent (c)], respectively, and D,E,F,G and H represent the limit compositions of the present invention.

That is, D is 90 w/w % of the constituent (a), 5 w/w % of the constituent (b) and 5 w/w % of the constituent (c); E: 55 w/w %, 40 w/w % and 5 w/w %; F: 30 w/w %, 40 w/w % and 30 w/w %; G: 30 w/w %, 30 w/w % and 40 w/w % and H: 55 w/w %, 5 w/w % and 40 w/w % respectively. The compositions in the pentagon area which is formed by connecting D - H are included in the present invention.

DESCRIPTION OF THE PREFERRED EMBODIMENTS

The base of the block copolymers used in the present invention is a block copolymer comprising the intermediate block (90 to 60% by weight) which comprises a conjugated diene copolymer and the both terminal blocks (10 to 40% by weight) which comprise a polymer of an aromatic vinyl compound. As the polymer of an aromatic vinyl compound which constitutes the both terminal blocks, there can be mentioned polymers of styrene series such as polystyrene, poly-α-methylstyrene, poly-p-methylstyrene, polychlorostyrene and the like. The most preferred is polystyrene. Those polymers of styrene series having a number-averaged molecular weight of 5000 to 125,000 are suitable. As the polymer of conjugated diene series which constitutes the intermediate block, there can be mentioned polybutadiene, polyisoprene, polychloroprene and the like. Polybutadiene and polyisoprene are preferred. Those polymers of conjugated diene series having a number-averaged molecular weight of 10,000 to 30,000 are suitable.

The block copolymers used in the present invention are hydrogenated products of the above-mentioned block copolymers which are commercially available and obtainable in a known method.

The term of "ratio of hydrogenation" as used in the specification means a ratio of an observed hydrogenated double bond in a theoretically hydrogenable double bond in either the terminal block moiety or the intermediate block moiety. It is necessary that the ratio of hydrogenation of both terminal blocks is 10% or less and the ratio of hydrogenation of the intermediate block is 90% or more.

Above all, it is preferable that the ratio of hydrogenation of the intermediate block is 95% or more. This is because, for example, in the case wherein the intermediate block is polybutadiene, the hydrogenation product has a constitution of ethylene/butylene copolymer and, in the case wherein the intermediate block is polyisoprene, the hydrogenation product has a constitution of ethylene/propylene copolymer. That is, the high hydrogenation ratio of the intermediate block results in improvement in the thermal resistance and the weathering resistance of the whole block copolymer. Above all, it results in the superior thermal resistance (high-temperature strength) of the compositions of the present invention. In the block copolymers used in the present invention, both terminal blocks act as their hardening component and the intermediate block acts as their softening component.

In case the terminal blocks are less than 10% by weight of the copolymer, the hardness and the strength of the copolymer are insufficient. In case the terminal blocks are more than 40% by weight of the copolymer, its softness is insufficient. It is preferred that the both terminal blocks are 15 to 25% by weight of the copolymer.

The block copolymers used in the present invention are easily available under the names KRATON G-1650, KRATON G-1652, KRATON G-1657, KRATON G-1658 (all Shell Chemical's products) and the like. These block copolymers may be used individually or in combination.

As the polypropylene used in the present invention, an isotactic polypropylene or a copolymer comprising such isotactic polypropylene having a melting point of 150° C. or higher as the main component, which is generally used as molding material, may be used as it is. As the copolymer comprising isotactic polypropylene, a block or random copolymer of propylene and an α-olefin such as ethylene, 1-butene or the like, may be used. However, for maintaining softness of the compositions of the present invention, a soft one, especially a random copolymer, is preferred. It is necessary for maintaining high-temperature strength of the compositions of the present invention that the melting point of the isotactic polypropylene or the copolymer comprising it as the main component is 150° C. or higher. Although the effect of this polypropylene constituent in the compositions of the present invention resides mainly in improvement of the high-temperature strength, it is considered that the polypropylene constituent has also an effect of improving the molding-characteristic of the compositions in cooperation with the ethylene/acrylate copolymer constituent as described below. With the block copolymers of the present invention alone, it is difficult to prepare pellet, tube, sheet, etc. by extrusion and mold goods such as bottle, etc. by blow molding. By incorporation of the polypropylene constituent and the ethylene/acrylate copolymer constituent, however, the molding-characteristic of the compositions is significantly improved. Moreover, it is also advantageous that the polypropylene constituent has a good compatibility with the block copolymers and polyblend can be effected with good transparency.

Next, it is necessary that the ethylene/acrylate copolymer used in the present invention has an acrylate content of 5% or more. With an acrylate content of less than 5%, transparency of the compositions lowers and softness of the compositions becomes insufficient. As the acrylate in the ethylene/acrylate copolymer used in the present invention, there can be mentioned methyl acrylate, ethyl acrylate, butyl acrylate, 2-ethylhexyl acrylate and the like, and metacrylates corresponding thereto. Most preferrred is ethyl acrylate. Although it is considered that the effect of the ethylene/acrylate constituent in the compositions of the present invention resides in improvement of the molding-characteristic, maintenance of the low-temperature softness, and the like, as described above, an especial effect brought about by incorporation of this constituent is that the transparency of polyblend systems of the block copolymer constituent is more improved. Further, it is advantageous that the content of the expensive block copolymers in the compositions can be reduced by incorporating the ethylene/acrylate copolymer which is rich in softness. By the way, the synthetic resin compositions containing the ethylene/acrylate copolymer is superior in the low-temperature softness and the high-temperature strength, and also in the behavior against hydrolysis, as compared with similar synthetic resin compositions containing an ethylene/vinyl acetate copolymer.

Although the composition range of the main constituents of the resin compositions of the present invention is shown in FIG. 1, it is necessary that the content of the block copolymers is from 30 to 90% by weight. In case it is less than 30% by weight, the softness and the transparency would be insufficient. In case it is more than 90% by weight, the high-temperature strength and the molding-characteristic would be insufficient. Most preferred content is from 40 to 80% by weight. As for the polypropylene constituent, it is necessary that the content is from 5 to 40% by weight. In case it is less than 5% by weight, the high-temperature strength and the molding-characteristic would be insufficient. In case it is more than 40%, the softness and the transparency would be insufficient. Especially preferred is from 10 to 30% by weight. The content of the ethylene/acrylate copolymer is requested to be from 5 to 40% by weight. In case it is less than 5% by weight, the molding-characteristic, the softness and the transparency would be insufficient. In case it is more than 40% by weight, the high-temperature strength and the transparency would be insufficient. Especially preferred is from 10 to 30% by weight.

Synthetic resin compositions comprising 40 to 80% by weight of the block copolymer (a), 10 to 30% by weight of the isotactic polypropylene or a copolymer comprising it as the main component (b) and 10 to 30% by weight of the ethylene/acrylate copolymer (c) are good in softness and transparency and superior in high-temperature strength and molding-characteristic. Such composition range is preferred.

The compositions of the present invention have an excellent softness, that is, a Shore-hardness of 45 or less, and a good transparency, that is, a light transmission percentage of 70% or more. They have also excellent high-temperature strength and molding-characteristic. The terms "excellent high-temperature strength" used here mean that a sheet made of them keeps its shape even when it is left to stand for 15 minutes in an oven at 125° C. and maintains such strength as it may not be cut off by giving a load of 1.4 kg/cm² at the same temperature. The terms "excellent molding-characteristic" mean that injection molding, extrusion molding and blow molding can be effected with a conventional molding machine.

While the resin compositions of the present invention satisfy those various properties as mentioned above, they have a superior low-temperature property such as a brittle point temperature of about −70° C. and a high strength such as a tensile strength of about 300 kg/cm². Moreover, they do not cause any sanitary troubles because they do not contain any plasticizer. Further, they are characterized also by their small water absorption, almost no weight loss on heating and less secular change in quality.

Besides the above-mentioned indispensable main resin constituents, the compositions of the present invention may contain according to the use thereof various plasticizers, anti-blocking agents, sealing improvers, thermo-stabilizers, antioxidants, ultraviolet absorbing agents, lubricants, crystal nucleus agents, coloring agents, etc. in an amount not retarding the softness, transparency, high-temperature strength, molding-characteristic and safeness. When they are used for preparing food-packing material or medical applicances, it is favorable not to incorporate such additives as plasticizers.

The compositions of the present invention may be molded in a usual manner. That is, various kinds of materials prescribed in accordance with the compositions are first mixed by a mixer, blender or the like, the mixture is further milled by hot rolls, and then sheet is manufactured by a press. Sheets, blocks, shapes, tubes, nets, etc. may be also manufactured by extrusion molding, from pellets which are prepared by an extruding machine. Various kinds of parts, bottles, etc. may be manufactured also by injection molding or blow molding, from the pellets. Various kinds of mold goods prepared or manufactured from the compositions of the present invention may be subjected to secondary processing such as cutting, painting, adhesion, printing or the like.

Although the compositions of the present invention, being provided with various characteristics as mentioned above, can be used in various fields such as the fields of general industrials, domestic goods and the like, they are incomparably useful in the fields of food-packing materials and medical applicances where sterilization at high temperature is requested, by virtue of their excellent high-temperature strength and non-toxicity. Further, the compositions of the present invention are especially suitable for manufacturing medical bags such as blood bag; infusion bag, bag for liquor for artificial dialysis, etc., since they are provided with sanitary safeness in addition to the excellent softness, transparency, high-temperature strength and molding-characteristic.

In the following, the present invention is explained by Examples. The invention, however, shall not be limited to these Examples.

EXAMPLE 1

A blended resin composition having the following formula was processed through two rolls into a raw sheet. A sheet having a thickness of about 0.4 m/m was prepared from the raw sheet by compression molding, and the physical properties thereof were determined.
Block copolymer:
  KRATON G-1650 (Shell Chemical's product) 40% by weight
  KRATON G-1657 (Shell Chemical's product) 20% by weight
Polypropylene:
  A random copolymer of isotactic polypropylene and ethylene having a melting point of 165° C. (This random copolymer contains about 5% of ethylene. The same random copolymer was used also in the following Examples.) 20% by weight
Ethylene/acrylate copolymer:
  NVC-6220 (Nihon Unicar's product) 20% by weight
  KRATON G-1650 and KRATON G-1657 are copolymers whose both terminal blocks are constituted by polystyrene and whose intermediate hydrogenated block is constituted by ethylene/butylene copolymer, the ratio of the former to the latter being 28/72 in G-1650 and 14/86 in G-1657. The NVC-6220 is an ethylene/ethyl acrylate copolymer having an ethyl acrylate content of 7%.

Physical data obtained are shown in the following. The tensile strength and the tensile elongation were determined according to JIS K6732, the light transmission (Total luminance transmission) percentage and the haze according to ASTMD-1003 or JIS K6714, and the Shore-hardness according to ASTMD-1706. The high-temperature strength was determined by the shape-keeping property observed by leaving a sheet to stand for 15 minutes in an oven at 125° C. and the state of deformation observed by giving a load of 1.4 kg/cm² to sheet at the same temperature.

Tensile strength: 310 kg/cm²
Tensile elongation: 720%
Light transmission percentage: 84%
Haze: 7%
Shore hardness: D-34
High-temperature strength
  Shape-keeping: All right
  Deformation ratio: 45%

EXAMPLE 2

Various sheets were prepared according to the same process as Example 1, while changing the composition or formula for the resin. Physical data for the sheets were determined. The results obtained are shown in the following table:

EXAMPLE 3

A composition having the following formula was blended by a blender and then extruded by an extruder to prepare pellets.

(a) KRATON G-1650: 25% by weight
(b) KRATON G-1657: 25% by weight
(c) Isotactic polypropylene random copolymer having a melting point of 165° C.: 25% by weight
(d) DPDJ-6182 (Nihon Unicar's product; EEA copolymer having an ethyl acrylate content of 15%): 25% by weight
(e) Stearic acid: 0.2 parts per 100 parts of the above resin
(f) Synthetic rosin: 3 parts per 100 parts of the above resin From the pellets, a sheet having a thickness of about 0.4 m/m was prepared by extrusion through a die of coat-hanger type and its properties were determined. The results are shown in the following table. The modulus of elasticity is a value determined by Vibron dynamic elasto-viscosimeter at a frequency of 110 cycle.

| No. | KRATON G-1650 | KRATON G-1657 | PP | EEA | Tensile Strength (kg/cm²) | Elongation (%) | Light transmission percentage (%) | Haze (%) | Shore hardness (%) | High-temperature strength Shape-keeping | Deformation ratio |
|---|---|---|---|---|---|---|---|---|---|---|---|
| | | | | EA 7% | | | | | | | |
| 1 | 35 | 25 | *20 | 20 | 300 | 800 | 84 | 7 | 32 | All right | 50 |
| 2 | 35 | 25 | *30 | 10 | 320 | 500 | 78 | 12 | 41 | " | 20 |
| 3 | 35 | 25 | *10 | 30 | 290 | 820 | 82 | 8 | 30 | " | 70 |
| 4 | 60 | 0 | *10 | 30 | 310 | 700 | 81 | 8 | 38 | " | 48 |
| 5 | 40 | 20 | °*20 | 20 | 320 | 660 | 82 | 9 | 37 | " | 45 |
| | | | | EA 15% | | | | | | | |
| 6 | 40 | 20 | *20 | 20 | 300 | 720 | 85 | 6 | 31 | " | 55 |
| 7 | 20 | 30 | *25 | 25 | 290 | 760 | 77 | 12 | 35 | " | 60 |
| 8 | 10 | 35 | *30 | 25 | 300 | 660 | 72 | 16 | 37 | " | 66 |
| 9 | 10 | 35 | *25 | 30 | 250 | 780 | 78 | 11 | 34 | " | 80 |
| 10 | 60 | 20 | *10 | 10 | 300 | 620 | 83 | 7 | 33 | " | 62 |
| 11 | 60 | 20 | *4 | 16 | 290 | 640 | 85 | 6 | 31 | " | cut |
| 12 | 15 | 30 | *10 | 45 | 290 | 630 | 68 | 17 | 38 | Considerably deformed | cut |
| 13 | 65 | 30 | *4 | 1 | 300 | 680 | 85 | 5 | 32 | All right | cut |
| 14 | 0 | 0 | °100 | 0 | 350 | 280 | 76 | 11 | 75 | " | 58 |
| 15 | 0 | 0 | °0 | 100 | 160 | 800 | 87 | 4 | 33 | Completely softened | cut |

*Random copolymer was used.
°*Homopolymer was used.

In the above table, Nos. 1 to 10 are within the range of composition and physical data of the present invention and have satisfactory physical properties, while Nos. 11 to 15 are outside the composition range of the present invention and show unsatisfactory physical data in some point or other.

As referential example, a sheet of soft polyvinyl chloride containing 52 parts of di-2-ethylhexyl phthalate as plasticizer was also prepared and its physical properties were determined. The results are shown in column B of the table.

The heat-seal strength given in the table is a value of strength against peeling, which was determined with respect to a sheet heat-sealed by a heat-seal bar with a pressure of 6 kg/cm² for 3 seconds at 200° C. (185° C. for the case B).

| | | Unit | A | B |
|---|---|---|---|---|
| Composition | | | Example 3 | soft polyvinyl chloride |
| Specific gravity | | | 0.91 | 1.30 |
| Tensile strength | | kg/cm² | 310 | 210 |
| Elongation | | % | 680 | 290 |
| Modulus of elasticity | −30° C. | | $1.2 \times 10^3$ | $1.2 \times 10^4$ |
| | 20° C. | kg/cm² | $7.0 \times 10^2$ | $6.6 \times 10^2$ |
| | 80° C. | | $2.2 \times 10^2$ | $4.0 \times 10^1$ |
| Light transmission percentage | | % | 83 | 90 |
| Haze | | % | 6 | 3 |
| Shore hardness | | D | 31 | 28 |
| High-temperature | Shape-keeping | | | |

-continued

|  | Unit | A | B |
|---|---|---|---|
| strength (Deformation ratio) | % | excellent 25 | excellent 76 |
| Weight loss on heating | 80° C. × 6 hrs., % | 0.0 | 1.0 |
| Water permeability | room temperature, 12 days, % | 0.6 | 2.1 |
| Heat-seal strength | kg/25 m/m | 9.8 | 9.2 |

A bag made of the sheet A and a bag made of the sheet B were filled with distilled water and sterilized at 121° C. for 1 hour in a steam sterilizer. Immediately after being taken out, both bags were not destroyed. Though they were whitened to some degree, the bag made of A has recovered within relatively short time.

Further, the sheet A was tested according to the Japanese pharmacopoeia, 10th revision, general examination method 42; examination method for plastic containers for infusion. The results obtained are shown in the following table. The results were very good.

| Item of examination | Result |
|---|---|
| Heavy metal | not detected |
| Lead | " |
| Tin | " |
| Cadmium | " |
| Vinyl chloride | " |
| Residue on exposing to strong heat (%) | 0.04 |
| [Eluate examination] | |
| Properties | all right |
| Foaming | " |
| pH | 0.2 |
| Chloride | not detected |
| Sulfate | " |
| Phosphate | " |
| Ammonium | " |
| Zinc | " |
| Potassium permanganate-reducing substance | 0.2 ml |
| Evaporation residue | 0.1 mg |
| Ultra Violet absorption spectrum 220–241 nm | 0.05 |
| 241–350 nm | 0.04 |

EXAMPLE 4

A composition having the following formula was blended by a blender and then extruded by an extruder to prepare pellets which were called A. For comparison's sake, pellets were prepared according to the same process except that an ethylene/vinyl acetate copolymer with a vinyl acetate content of 15% was used instead of DPDJ-6182. The pellets were called B.

(a) KRATON G-1650: 30% by weight
(b) KRATON G-1657: 30% by weight
(c) Polypropylene random copolymer having a melting point of 165° C.: 20% by weight
(d) DPDJ-6182: 20% by weight
(e) Stearic acid: 0.2 parts per 100 parts of the above resin From the pellets A and B, sheets having a thickness of about 0.35 m/m were prepared by extrusion through a die of coat-hanger type and their properties were determined. The results are shown in the following table.

|  | Unit | A | B |
|---|---|---|---|
| Surface condition of extruded sheet |  | excellent gloss slightly rough | good gloss considerably rough surface |
| Specific gravity |  | 0.91 | 0.91 |
| Tensile strength | kg/cm$^2$ | 320 | 280 |
| Elongation | % | 740 | 760 |
| Modulus of elasticity −30° C. |  | $1.0 \times 10^3$ | $2.8 \times 10^3$ |
| 20° C. |  | $6.6 \times 10^2$ | $6.8 \times 10^2$ |
| 80° C. |  | $2.0 \times 10^2$ | $1.4 \times 10^2$ |
| Light transmission percentage | % | 85 | 81 |
| Haze | % | 5 | 7 |
| Shore hardness | D | 30 | 32 |
| High-temperature Shape-keeping strength | % | excellent | excellent |
| Deformation ratio |  | 32 | 125 |
| Weight loss on heating | 80° C. × 6 hrs., % | 0.0 | 0.0 |
| Water permeability | room temp., 12 days; % | 0.5 | 0.8 |
| Oxygen permeability |  | 530 | 810 |
| Heat-seal strength | kg/25 mm | 9.6 | 9.7 |
| Destruction ratio after steam sterilization | * | 0/5 | 2/5 |

*2/5 means that two bags among five were destroyed. Both A and B were whitened to some degree, just after being taken out after steam sterilization. However, A recovered within a shorter time as compared with B.

As is apparent from the above, A(EEA) is superior to B(EVA) in various respects. Particularly on respects of surface conditions of sheet, low-temperature softness, high-temperature strength, transparency, water-resisting property, oxygen permeability, etc., A shows significant superiority to B. The excellent low-temperature softness provides such advantage that bags for disposable medical fluid are scarcely destroyed even on transportation or treatment in cold district and medical fluid may easily be poured into the bags by the pressure of the open air. The low oxygen permeability prevents degeneration by oxidation of the contents of bags, such as medical fluid containing amino acids, and the low water permeability prevents degeneration by moisture dispersion of the contents of bags.

EXAMPLE 5

A composition having the following formula was blended by a blender and then extruded by an extruder to prepare pellets.

(a) KRATION G-1657: 40% by weight
(b) Polypropylene random copolymer having a melting point of 165° C.: 30% by weight (c) DPDJ-6182: 30% by weight
(d) Stearic acid: 0.2 parts per 100 parts of the above resin From the pellets, a sheet having a thickness of about 0.4 mm was prepared by extrusion through a die of coat-hanger type and its properties were determined. The results are given in the following. The sheet showed excellent properties except that its light transmission percentage was slightly inferior.

Tensile strength: 290 kg/cm$^2$
Tensile elongation: 660%
Holophotal transmission percentage: 80%
Haze 10%
Shore hardness D-21
High-temperature strength
Shape-keeping: all right
Deformation ratio 52%

A tube having an outer diameter of 4 mm and an inner diameter of 2 mm was prepared also from the pellets. The tube was soft, sufficient in transparency and gloss, and scarcely bent or folded.

EXAMPLE 6

A composition having the following formula was blended by a blender and then extruded by an extruder to prepare pellets.
(a) KRATON G-1652: 30% by weight
(b) KRATON G-1657: 22% by weight
(c) Polypropylene random copolymer having a melting point of 165° C.: 25% by weight
(d) PE 2205 (Gulf Oil Chemical's product; ethylene-/methyl acrylate copolymer): 23% by weight
(e) Stearic acid: 0.2 parts per 100 parts of the above resin Although KRATON G-1652 has a composition similar to that of KRATON G-1650, its molecular weight is low and its fluidity is good.

From the pellets, a sheet having a thickness of about 0.4 mm was properties were determined. The results are shown in the following.

Tensile strength: 310 kg/cm$^2$
Tensile elongation: 740%
Holophotal transmission percentage: 83%
Haze: 7%
Shore hardness: D-31
High-temperature strength
  Shape-keeping: all right
  Deformation ratio: 38%

A tube having an outer diameter of 8 mm and an inner diameter of 6 mm was prepared also from the pellets.

The tube was good in softness, transparency, surface gloss and other respects.

What I claim is:
1. A synthetic resin composition comprising
  (a) 40 to 80% by weight of a block copolymer whose both terminal blocks comprise a polymer of an aromatic vinyl compound and whose intermediate block comprises a polymer of conjugated diene series, said terminal blocks constituting 10 to 40% by weight of the copolymer and being hydrogenated in a ratio of 10% or less and said intermediate block constituting 90 to 60% by weight of the copolymer and being hydrogenated in a ratio of 90% or more;
  (b) 10 to 30% by weight of an isotactic polypropylene or a copolymer comprising such isotactic polypropylene as its main component having a melting point of 150° C. or higher, and
  (c) 10 to 30 % by weight of an ethylene-acrylate copolymer whose acrylate content is 5 w/w % or more.
2. A synthetic resin composition as claimed in claim 1, in which the component (a) is a hydrogenated product of a block copolymer whose both terminal blocks are polystyrene, poly-α-methylstyrene, poly-p-methylstyrene or polychlorostyrene and whose intermediate block are polybutadiene, polyisoprene or polychloroprene.
3. A synthetic resin composition as claimed in claim 2, in which the terminal block is polystyrene and the intermediate block is polybutadiene.
4. A synthetic resin composition as claimed in claim 1 in which the copolymer comprising isotactic polypropylene is an isotactic random copolymer of propyleneethylene or butene.
5. A synthetic resin composition as claimed in claim 1 in which the ethylene-acrylate copolymer is a copolymer of ethylene with methyl acrylate, ethyl acrylate, butyl acrylate or 2-ethylhexyl acrylate.
6. Food packing materials or medical appliances comprising the synthetic resin composition of claim 1.
7. Medical bags for blood bag infusion and for liquor for artificial dialysis comprising the synthetic resin composition of claim 1.
8. A synthetic resin composition as claimed in claim 1, wherein component (c) is ethylene-ethylacrylate copolymer.

* * * * *